United States Patent [19]
Mertens

[11] Patent Number: 5,947,927
[45] Date of Patent: Sep. 7, 1999

[54] CONVERTIBLE CATHETER HAVING A SINGLE PROXIMAL LUMEN

[75] Inventor: Steven P. Mertens, Plymouth, Minn.

[73] Assignee: SciMed Life Systems, Inc., Maple Grove, Minn.

[21] Appl. No.: 09/046,031

[22] Filed: Mar. 23, 1998

[51] Int. Cl.$^6$ .................................................. A61M 29/00
[52] U.S. Cl. ............................................ 604/96; 604/102
[58] Field of Search ................................ 604/96, 97, 102, 604/93, 164, 167, 169, 912, 917; 606/194, 192

[56] References Cited

U.S. PATENT DOCUMENTS

| | | |
|---|---|---|
| 3,460,541 | 8/1969 | Doherty . |
| 3,707,151 | 12/1972 | Jackson . |
| 3,889,686 | 6/1975 | Duturbure . |
| 3,890,977 | 6/1975 | Wilson . |
| 3,970,089 | 7/1976 | Saice . |
| 4,194,513 | 3/1980 | Rhine et al. . |
| 4,299,226 | 11/1981 | Banka . |
| 4,364,392 | 12/1982 | Strother et al. . |
| 4,413,989 | 11/1983 | Schjeldahl et al. . |
| 4,423,725 | 1/1984 | Baran et al. . |
| 4,425,919 | 1/1984 | Alston, Jr. et al. . |
| 4,445,892 | 5/1984 | Hussein et al. . |
| 4,554,929 | 11/1985 | Samson et al. . |
| 4,573,470 | 3/1986 | Samson et al. . |
| 4,581,017 | 4/1986 | Sahota . |
| 4,606,347 | 8/1986 | Fogarty et al. . |
| 4,616,653 | 10/1986 | Samson et al. . |
| 4,641,654 | 2/1987 | Samson et al. . |
| 4,646,742 | 3/1987 | Packard et al. . |
| 4,654,025 | 3/1987 | Cassou et al. . |
| 4,655,746 | 4/1987 | Daniels et al. . |
| 4,723,550 | 2/1988 | Bales et al. . |
| 4,748,982 | 6/1988 | Horzewski et al. . |
| 4,762,129 | 8/1988 | Bonzel . |
| 4,763,654 | 8/1988 | Jang . |
| 4,771,777 | 9/1988 | Horzewski et al. . |
| 4,790,315 | 12/1988 | Mueller, Jr. et al. . |
| 4,798,193 | 1/1989 | Giesy et al. . |
| 4,798,594 | 1/1989 | Hillstead . |
| 4,813,934 | 3/1989 | Engelson et al. . |
| 4,817,613 | 4/1989 | Jaraczewski et al. . |
| 4,838,268 | 6/1989 | Keith et al. . |
| 4,846,174 | 7/1989 | Willard et al. . |
| 4,846,193 | 7/1989 | Tremulis et al. . |

(List continued on next page.)

FOREIGN PATENT DOCUMENTS

| | | |
|---|---|---|
| A-10067/88 | 7/1988 | Australia . |
| 0 513 818 A1 | 11/1992 | European Pat. Off. . |
| WO 92/00775 | 1/1992 | WIPO . |
| WO 92/13589 | 8/1992 | WIPO . |
| WO 93/11826 | 6/1993 | WIPO . |
| WO 94/11047 | 5/1994 | WIPO . |

Primary Examiner—Wynn Wood Coggins
Assistant Examiner—LoAn H. Thanh
Attorney, Agent, or Firm—Crompton, Seager & Tufte, LLC.

[57] ABSTRACT

A convertible intravascular catheter assembly having a single proximal lumen while incorporating the benefits of a single operator exchange catheter and an over-the-wire catheter. The catheter includes a first elongate shaft having a lumen therethrough for slidably receiving a guide wire or stylet. The first elongate shaft extends the length of the catheter, while a second elongate shaft is coaxially disposed over a distal portion of the first elongate shaft to form a second lumen therebetween. An inflatable balloon is sealingly connected proximate the distal end of the second elongate shaft, and sealingly connected proximate the distal end of the second elongate shaft. A fluid connection communication between the first lumen and second lumen are provided and the seal assembly is disposed within the first lumen distal of the means for fluid communication. An intermediate guide wire port is provided distal of the seal assembly and the combination allows the use of a single lumen proximal of the seal assembly to operate both as an inflation lumen and a guide wire lumen when used in the over-the-wire mode.

24 Claims, 2 Drawing Sheets

U.S. PATENT DOCUMENTS

| | | |
|---|---|---|
| 4,848,344 | 7/1989 | Sos et al. . |
| 4,877,031 | 10/1989 | Conway et al. . |
| 4,892,519 | 1/1990 | Songer et al. . |
| 4,898,577 | 2/1990 | Badger et al. . |
| 4,906,241 | 3/1990 | Noddin et al. . |
| 4,928,693 | 5/1990 | Goodin et al. . |
| 4,932,413 | 6/1990 | Shockey et al. . |
| 4,932,959 | 6/1990 | Horzewski et al. . |
| 4,944,745 | 7/1990 | Sogard et al. . |
| 4,964,409 | 10/1990 | Tremulis . |
| 4,967,753 | 11/1990 | Haase et al. . |
| 4,976,720 | 12/1990 | Machold et al. . |
| 4,986,814 | 1/1991 | Burney et al. . |
| 4,988,356 | 1/1991 | Crittenden et al. . |
| 4,994,027 | 2/1991 | Farrell . |
| 4,998,917 | 3/1991 | Gaiser et al. . |
| 5,003,990 | 4/1991 | Osypka . |
| 5,007,901 | 4/1991 | Shields . |
| 5,015,231 | 5/1991 | Keith et al. . |
| 5,019,042 | 5/1991 | Sahota . |
| 5,026,607 | 6/1991 | Kiezulas . |
| 5,031,636 | 7/1991 | Gambale et al. . |
| 5,032,113 | 7/1991 | Burns . |
| 5,035,705 | 7/1991 | Burns . |
| 5,040,548 | 8/1991 | Yock . |
| 5,045,061 | 9/1991 | Seifert et al. . |
| 5,046,497 | 9/1991 | Millar . |
| 5,047,018 | 9/1991 | Gay et al. . |
| 5,047,045 | 9/1991 | Arney et al. . |
| 5,057,092 | 10/1991 | Webster, Jr. . |
| 5,061,267 | 10/1991 | Zeiher . |
| 5,061,273 | 10/1991 | Yock . |
| 5,066,285 | 11/1991 | Hillstead . |
| 5,078,681 | 1/1992 | Kawashima . |
| 5,085,636 | 2/1992 | Burns . |
| 5,090,958 | 2/1992 | Sahota . |
| 5,114,403 | 5/1992 | Clarke et al. . |
| 5,120,308 | 6/1992 | Hess . |
| 5,125,905 | 6/1992 | Wright et al. . |
| 5,135,494 | 8/1992 | Engelson et al. . |
| 5,135,535 | 8/1992 | Kramer . |
| 5,141,518 | 8/1992 | Hess et al. . |
| 5,147,377 | 9/1992 | Sahota . |
| 5,154,725 | 10/1992 | Leopold . |
| 5,160,321 | 11/1992 | Sahota . |
| 5,171,221 | 12/1992 | Samson . |
| 5,171,222 | 12/1992 | Euteneuer et al. . |
| 5,171,298 | 12/1992 | Walker et al. . |
| 5,180,367 | 1/1993 | Kontos et al. . |
| 5,181,921 | 1/1993 | Makita et al. . |
| 5,209,728 | 5/1993 | Kraus . |
| 5,217,434 | 6/1993 | Arney . |
| 5,221,260 | 6/1993 | Burns et al. .............................. 604/99 |
| 5,256,144 | 10/1993 | Kraus et al. . |
| 5,290,247 | 3/1994 | Crittenden . |
| 5,304,198 | 4/1994 | Samson . |
| 5,324,259 | 6/1994 | Taylor et al. . |
| 5,348,537 | 9/1994 | Wiesner et al. . |
| 5,364,354 | 11/1994 | Walker et al. . |
| 5,364,376 | 11/1994 | Horzewski et al. . |
| 5,489,271 | 2/1996 | Andersen . |
| 5,490,837 | 2/1996 | Blaeser et al. ............................ 604/96 |
| 5,554,118 | 9/1996 | Jang ........................................ 604/102 |
| 5,626,603 | 5/1997 | Venturelli et al. ....................... 604/94 |
| 5,695,468 | 12/1997 | Lafontaine et al. . |
| 5,807,328 | 9/1998 | Briscoe ..................................... 604/96 |
| B1 4,762,129 | 7/1991 | Bonzel . |

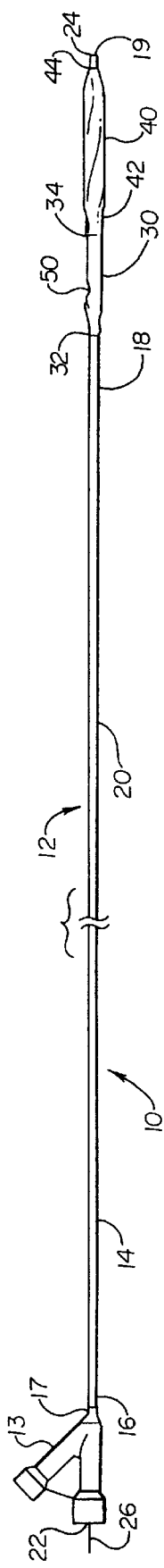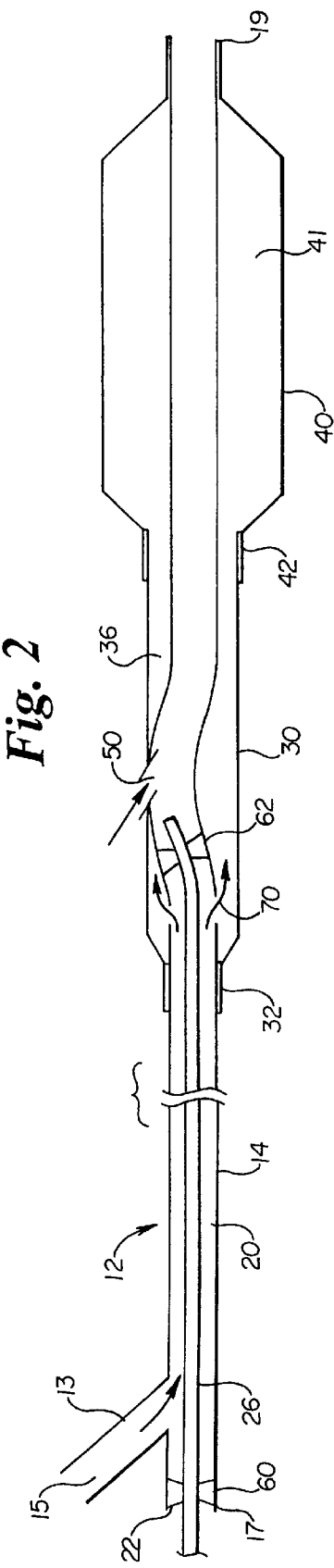

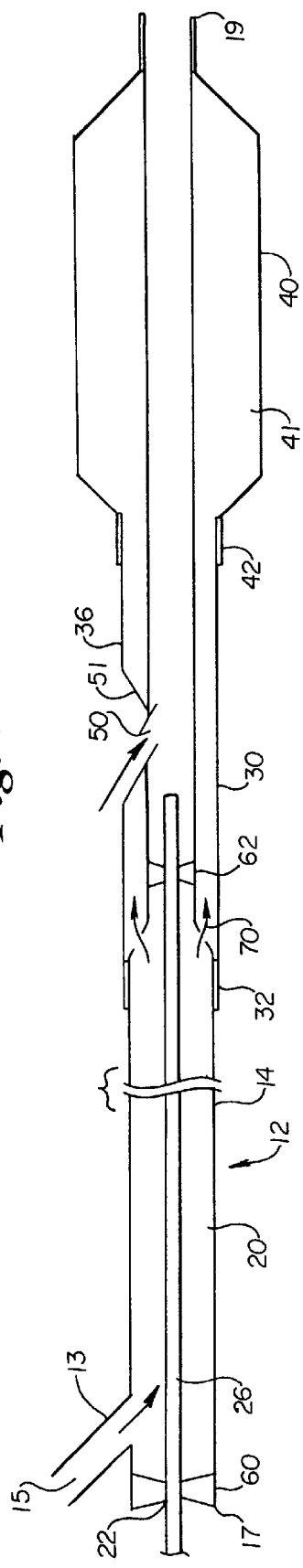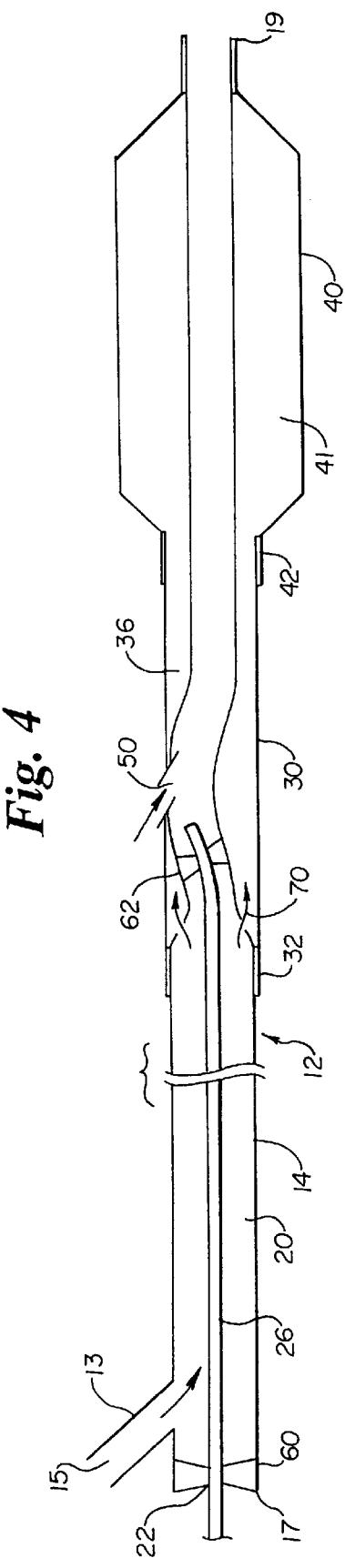

CONVERTIBLE CATHETER HAVING A SINGLE PROXIMAL LUMEN

TECHNICAL FIELD

This invention relates to the field of intravascular medical devices used in combination with guide members. More specifically, the present invention relates to an intravascular balloon dilatation catheter incorporating a single proximal lumen with full length and partial length guide wire lumen capability.

BACKGROUND OF THE INVENTION

Intravascular catheterization devices have proven to be useful and efficient for both therapeutic and diagnostic purposes. Intravascular therapeutic techniques, such as angioplasty, atherectomy, and laser irradiation, have been developed as alternatives to bypass surgery for treating vascular diseases or other conditions that occlude or reduce the lumen size of portions of a patient's vascular system. In particular, balloon angioplasty has proven to be a useful and in many circumstances a preferred treatment for obstructive coronary diseases. Also, intravascular diagnostic techniques, such as ultrasonic imaging and Doppler blood flow measurements, have been developed to measure or image the extent of an occlusion of a vessel (e.g., stenosis). The devices used to perform the aforementioned intravascular therapeutic and diagnostic techniques may be used together or in conjunction with more invasive techniques such as coronary surgery.

These intravascular therapeutic and diagnostic devices have achieved acceptance because of their effectiveness as well as the fact that they can be used in a minor surgical procedure that is relatively nondisruptive to the patient compared to coronary surgery. These devices rely on the positioning of a catheter into the vascular system of a patient via an incision at an accessible location which may be remote from the site of the occlusion or stenosis. For example, the accessible location may be the femoral artery at the groin. The intravascular device is then advanced through the incision via the femoral artery to a desired coronary distal site. The distal sites into which the device may be advanced include the coronary arteries, branch vessels stemming from the external carotid artery such as the occipital and the arteries leading to the vessels of the head and brain, splenic, and the inferior mesenteric and renal arteries leading to the organs of the thorax as well as other vessels.

Because of the small size of some of these vessels and the tortuous passages through the vessels, positioning of a catheter device through a patient's vasculature can be a difficult and time consuming task requiring considerable skill on the part of the physician. For example, in order to perform an angioplasty dilation, the angioplasty balloon catheter must be positioned across the stenosis in the arterial site. The stenosis may be located in a tortuous portion of the coronary vasculature and, furthermore, the obstructive arterial disease may impede crossing the stenosis with the balloon portion of the angioplasty catheter. Thus, not all arterial obstructions can be successfully treated by present intravascular balloon catheter procedures because some arterial obstructions are not readily accessible to a balloon dilation catheter. Accordingly, there is often a need for intravascular catheters of very low profile that can be positioned in narrow, tortuous regions of a person's vasculature.

Another important consideration relating to intravascular procedures, such as angioplasty, relates to the exchange of various devices used to perform the procedures. Intravascular therapeutic and diagnostic devices come in various types and sizes suitable for the vessel size and location in which the treatment is to be performed. Sometimes, it becomes necessary to exchange a first therapeutic device for one of a different size after an unsuccessful attempt has been made to position the first device in the appropriate location. It may also become necessary to exchange therapeutic devices after the first device is successfully positioned in the desired location. This may be necessitated because it becomes apparent that the first device is the wrong size or configuration, or because it is determined that additional therapeutic or diagnostic procedures with a different size or type of device is required.

Several different types of catheter constructions have been developed for positioning intravascular therapeutic or diagnostic catheters through a patient's vasculature. Two primary types of catheter constructions are the over-the-wire (OTW) type catheters and the single operator exchange (SOE) type catheters.

An over-the-wire type catheter, includes a central lumen through the entire length of the intravascular device that can accommodate a separate guide wire that is movable, and removable, in relation to the catheter to facilitate positioning the catheter in a remote vessel location over the guide wire. In the over-the-wire construction, the catheter typically includes a lumen adapted to receive the guide wire from a proximal end to the distal end of the device. The guide wire is initially loaded through the lumen of the over-the-wire catheter and extends out from the distal end thereof. Then, the guide wire and the intravascular catheter are advanced together and positioned in the vessel at the desired site. The guide wire may be advanced distally of the distal end of the catheter and steered, as necessary, to traverse tortuous passages of the vessel with the catheter subsequently advanced distally over the wire tracking the wires path. With the guide wire extending through the full length lumen, the guide wire provides some column support to the catheter shaft especially in the distal portion thereof This improves the pushability of the catheter. The guide wire may then be withdrawn proximally through the lumen of the catheter or may be left in place extending from the distal end of the catheter during the procedure.

The over-the-wire type intravascular catheter facilitates exchanges because a first catheter can be exchanged with a second catheter without removing the guide wire. This allows an exchange of catheters without having to repeat the difficult and time-consuming task of positioning the guide wire. In order to leave the distal end of the guide wire in place, it is preferred to maintain a hold on a proximal end portion of the guide wire during the exchange operation. One way to maintain such a hold is to use a guide wire having a sufficiently long length (e.g., 300 cm) so that the entire catheter can be completely withdrawn over the guide wire while maintaining a hold on a portion of the wire. A disadvantage of this method is that the long proximally extending portion of the guide wire may be in the way during the procedure. Another way to maintain a hold on a portion of the guide wire during an exchange operation is to use a guide wire extension. A disadvantage of this method is that not all guide wires are adapted to connect to an extension wire, and moreover, the step of connecting the guide wire to the extension wire can sometimes be tedious and difficult to perform.

A second type of catheter, which facilitates the exchange of a first catheter with a second catheter, is the single-operator exchange type construction. With the single-operator exchange type construction, a guide wire occupies a position adjacent and exterior to the intravascular catheter along proximal and intermediate portions of the catheter and enters into a short guide wire lumen of the catheter via an opening at a location close to a distal portion of the catheter. With this type of construction, the catheter can be positioned in the patient's vessel by positioning a guide wire in the desired location and advancing the catheter device over the wire. An advantage of the short guide wire lumen is that in the event it becomes necessary to exchange the catheter, the position of the guide wire can be maintained during withdrawal of the catheter without the use of a long guide wire (e.g., 300 cm) or an extension wire. Because the proximal end of the guide wire is exterior to the proximal end of the catheter, the proximal end of the guide wire can be held during withdrawal of the catheter so that the position of the distal end of the guide wire in the patient's vessel can be maintained. With this type of catheter, it is necessary that the distance from the distal end of the catheter to the proximal guide wire lumen entrance is less than the length of the guide wire that extends proximally out of the patient.

Although single operator exchange catheters make it easier to exchange catheters, the construction has two disadvantages. First, the guide running external to the catheter shaft do not provide any column support for the shaft nor does the shaft provide support for the wire if the wire is pushed distally to cross a lesion. Second, with the single operator exchange design, the guide wire can not be replaced while the catheter remains in the body.

Just as it is sometimes necessary to exchange an intravascular catheter, it may also become necessary to exchange the guide wire or otherwise assist in advancing the guide wire to the desired location in the vessel. After the guide wire and catheter are in the vessel, it may be determined that the size or shape of the guide wire is inappropriate for advancement to the desired position in a vessel. For example, the diameter of the guide wire may be too large for advancement past an extensive stenosis or occlusion in a vessel or for advancement in another relatively small vessel. The diameter of the guide wire may also be too small for effective advancement of the guide wire and catheter to the desired location in the vessel.

It may also be determined that the shape or construction of the guide wire is inappropriate for advancement of the guide wire to the desired position after the guide wire and catheter are in the vessel. For example, a distal portion of the guide wire is often bent a desired amount prior to insertion into the body of a patient to allow manipulation of the guide wire through various vessels. After the guide wire is in a vessel, it may be determined that a guide wire with a different "bend" is necessary to advance further to the desired position in the vessel or to advance into another vessel. The distal tip of the guide wire may also acquire an inappropriate bend during advancement of the guide wire in the vessel. For example, the distal tip of the guide wire may prolapse when movement of the tip is impeded and the guide wire is advanced further in the vessel.

When it is determined that the configuration of the guide wire is inappropriate for advancement in the vessel, the guide wire is typically exchanged for a guide wire having the desired configuration. With an over-the-wire type catheter, the guide wire can be withdrawn through the lumen of the catheter and a second guide wire can be installed while leaving the catheter in position. However, with a single-operator exchange type catheter, a guide wire exchange cannot readily be performed without withdrawing the catheter. Once the distal end of the first guide wire is withdrawn proximally from the proximal guide wire lumen opening of the catheter, a second guide wire cannot readily be positioned in the proximal guide wire lumen opening without also withdrawing the catheter so that the proximal guide wire lumen opening is outside the body of a patient.

To derive the benefits achieved from use of an over-the-wire catheter and a single operator exchange catheter, while overcoming the deficiencies of each, Scopton et al. disclose a convertible catheter assembly which includes both an over-the-wire capability and a single operator exchange capability. The Scopton et al. disclosure is made in PCT Application No. WO/17236, published on Oct. 15, 1992 and entitled "ADJUSTABLY STIFFENABLE CONVERTIBLE CATHETER ASSEMBLY". The disclosure of Scopton et al. is incorporated herein by reference. However, because the Scopton et al. design includes a separate proximal guide wire lumen and separate proximal inflation lumen, the overall profile of the catheter is larger than with a standard single operator exchange catheter which has only a single lumen in the proximal shaft portion. There is therefore a need in the art for a catheter design which incorporates the beneficial features of both a single operator exchange catheter and an over-the-wire catheter as discussed above, however, there is further a need for a design which reduces the overall profile of the catheter shaft by eliminating the need for two separate lumens over the entire length of the catheter assembly.

SUMMARY OF THE INVENTION

The present invention is directed to a convertible catheter assembly having a single proximal lumen. The catheter assembly, as disclosed herein, having a single proximal lumen which is utilized for both inflation fluid and a guide wire, reduces the overall profile of the catheter by having less pressure drop over a substantial portion of the length of the catheter. By having less pressure drop when inflation fluid is injected, the overall diameter of the catheter can be reduced while maintaining adequate inflation and deflation times when treating a vascular disease. As a convertible catheter, the present invention includes a full length guide wire lumen so that the catheter can be utilized as a standard over-the-wire catheter and an intermediate guide wire port into the full length guide wire lumen so that the catheter can be utilized as a single operator exchange catheter when desired. Thus, the catheter of the present invention provides the benefit of an over-the-wire catheter and a single operator exchange catheter in a single device while reducing the overall profile of the shaft for reaching more distal occlusions. To allow use of a single proximal lumen for use with a guide wire and simultaneous use as an inflation lumen, the present invention incorporates a proximal seal which is proximal of the point of injection of the inflation fluid and a distal seal which is distal of means for fluid communication between the lumen and a second distal inflation lumen.

In general, the convertible catheter assembly of the present invention includes a first elongate shaft having a proximal end and a distal end with a first lumen extending therethrough. This lumen is the full-length guide wire lumen of the present invention. The proximal end of the first elongate shaft includes a proximal guide wire port for slidably receiving a guide wire or stylet into the first lumen. A catheter of the present invention further includes a second elongate shaft having a proximal end and a distal end which is coaxially disposed over at least a portion of the distal portion of the first elongate shaft and forms a second lumen therebetween. This second lumen provides an inflation lumen for the distal section of the overall catheter assembly.

The second elongate shaft sealingly engages the first elongate shaft proximate the proximal end of the second elongate shaft. This can be accomplished by adhesively or heat bonding the interior surface of the second elongate shaft to the exterior surface of the first elongate shaft at the desired axial location.

A catheter of the present invention also includes an inflatable balloon having a proximal end sealingly connected proximate the distal end of the second elongate shaft, and a distal end sealingly connected proximate the distal end of the first elongate shaft. The balloon member provides an inflatable internal volume, which is in fluid communication with the lumen of the second elongate shaft. It is recognized that the second elongate shaft could constitute an integral extension of the proximal end of the balloon, or alternatively, the proximal end of the balloon may be adhesively or thermally bonded to a separate second elongate shaft.

The catheter assembly further includes means for fluid communication between the first lumen and the second lumen in combination with at least one seal assembly disposed within the first lumen distal of the means for fluid communication between the first and second lumen. The means for fluid communication between the first lumen and the second lumen can be simply at least one hole through the wall of the first elongate shaft into the annular space distal thereof created between the distal portion of the first elongate shaft and the second elongate shaft.

The seal assembly is sized to slidably receive a guide wire or stylet therethrough in sealing engagement. A preferred seal design includes an O-ring type seal which frictionally engages the stylet or guide wire when passed therethrough. It is also recognized, however, that the seal assembly could be sized to form a seal even when no guide wire or stylet is passed therethrough, yet allow a guide wire to push open the seal sufficient to slide therethrough. The seal can be formed by placing a bead of adhesive around the interior wall of the first elongate shaft at the desired location.

The convertible catheter assembly of the present invention also includes an intermediate guide wire port which is distal of the seal assembly and provides an exterior access point for a guide wire at an alternative location into the first lumen. In preferred embodiments, this guide wire port extends through both the wall of the second elongate shaft and the wall of the first elongate shaft at a point substantially distal of the proximal end of the catheter assembly. Because the port is distal of the seal assembly, no inflation fluid is present in that distal portion of the first lumen. In order for this to occur, however, a stylet or guide wire must be inserted into the proximal portion of the first lumen through the first seal assembly if such seals are not designed to prevent leakage when no guide wire or stylet is present.

In use, the catheter of the present invention is convertible, in that it can be utilized in a first mode which is an over-the-wire mode, or alternatively, in a second mode which is a single operator exchange mode. In use as an over-the-wire catheter, a guide wire is extended through the full length of the first lumen including out a distal end thereof so that the catheter can track over the guide wire to a lesion site to be treated. In this mode, the guide wire provides some column support for the catheter as it is moved distally to the point of treatment. Further, utilization of the full-length guide wire lumen allows exchange of guide wires if necessary. When the catheter is across a lesion, the balloon can be inflated by injecting inflation fluid proximate the proximal end of the catheter. With the guide wire in place, the seal assembly distal of the means for fluid communication between the first lumen and the second lumen substantially prevents leakage of inflation fluid into the lumen distal of the seal, and the inflation fluid passes into the second lumen to inflate the balloon. It is preferred that a second seal assembly is located in the first lumen proximal of the port for injecting inflation fluid. This seal assembly prevents substantial leakage of inflation fluid out the proximal end of the catheter around the guide wire inserted therethrough.

When operated in single operator exchange mode, a guide wire passes through the intermediate guide wire port into the first lumen and out the distal end of the catheter. In this mode, the catheter itself is readily exchanged without the use of a guide wire extension or long guide wire. In preferred embodiments, when the catheter is utilized in single operator exchange mode, the stylet or guide wire is inserted into the first lumen from the proximal end of the catheter to a point through the first seal assembly to prevent leakage of inflation fluid when the balloon is to be inflated. In the single operator exchange mode, the guide wire can still be exchanged by removing the stylet and inserting a full length guide wire into the first lumen after pulling back the single operator exchange wire to a point proximal of the intermediate guide wire port.

Accordingly, the present invention provides a convertible catheter assembly having a single proximal lumen which both allows operation in a single operator exchange and an over-the-wire mode, while reducing the overall profile of the catheter. The present invention, together with further objects and advantages, will be best understood by reference to the following Detailed Description taken in conjunction with the accompanying drawings.

BRIEF DESCRIPTION OF THE DRAWINGS

FIG. 1 is a schematic view of a convertible catheter assembly having a proximal, intermediate and distal guide wire port;

FIG. 2 is a schematic cross-sectional view of a distal portion and proximal portion of the catheter shown in FIG. 1;

FIG. 3 is a schematic cross-sectional view of an alternative distal section of the catheter of FIG. 2; and FIG. 4 is a schematic cross-sectional view of an alternative distal section of the catheter of FIG. 2.

DETAILED DESCRIPTION OF THE PREFERRED EMBODIMENT

The presently preferred embodiments and methodology described herein are applicable to coronary angioplasty procedures, and are specifically described in the context of dilatation balloon catheters. It should be understood, however, that the embodiments and methodology of the present invention may be adapted for use with other types of intravascular therapeutic devices, such as atherectomy catheters, as well as diagnostic catheters, such as ultrasonic catheters.

Referring to FIG. 1, a catheter of the present invention is depicted generally at 10. The intravascular apparatus 10 includes a balloon dilatation catheter 12 having a first elongate shaft 14. A proximal portion 16 of first elongate shaft 14 is adapted to extend outside the body of a patient during use, and a distal portion 18 of the shaft 14 is positioned intravascularly during use by manipulation of the proximal portion 16. The first elongate shaft has a proximal end 17 and a distal end 19 with a first lumen 20 extending therethrough (see, FIG. 2). The proximal end 17 of the first elongate shaft 14 includes a proximal guide wire port 22, while the distal end of the lumen 20 defines a distal guide wire port 24 with the lumen 20 sized to receive a guide wire 26 extending therethrough. By guide wire, it is also meant to include a stylet.

The convertible catheter assembly 12 depicted in FIG. 1 also includes a second elongate shaft 30 having a proximal end 32 and a distal end 34. The second elongate shaft 30 includes a second lumen 36 extending therethrough (see, FIG. 2). The second elongate shaft 30 is preferably generally coaxially disposed over a distal portion of the first elongate shaft 14.

The catheter assembly of FIG. 1 further includes an inflatable balloon 40 which has a proximal end 42 sealingly connected proximate the distal end 34 of the second elongate shaft 30. The balloon has a distal end 44 sealingly connected proximate the distal end 19 of the first elongate shaft 14. Finally, the catheter assembly 12 of FIG. 1 includes an intermediate guide wire port 50 which extends into the first lumen for receiving a guide wire therein to the distal guide wire port 24 when the catheter is utilized in a single operator exchange mode. The balloon 40 of the present invention can be formed from a polyolefin co-polymer or other polymer material. Specific balloon materials can include, polyolefin copolymers, polyether block amides, such as PEBAX, nylon, polyethylene terephthalate (PET) or ARNITEL (available from DSM Engineering Plastic Products, Reading, PA. Preferably, the balloon 40 has a proximal neck portion defining a proximal opening or a distal neck portion defining a distal opening. It is, however, recognized that the proximal neck portion can be extended to integrally form the second elongate shaft 30 of the present invention. However, it is preferred that the second elongate shaft is a separate tubular member which has different flexibility characteristics that the balloon material. The balloon can be adhesively or thermally bonded to the respective elongate shafts as is well known in the art.

Now referring to FIGS. 2–4, schematic cross sections of the proximal and distal sections of the catheter assembly 12 arc depicted. The embodiments in FIGS. 2–4 depict alternative structures for accomplishing the goal of the present invention, namely, to provide a convertible catheter assembly 12 which can be utilized both in a single operator exchange mode and an over-the-wire mode, while having a single proximal lumen 20 which functions as an over-the-wire guide wire lumen and an inflation lumen. The various embodiments of FIGS. 2–4 depict alternative distal portion designs which provide a transition from a single proximal guide wire lumen to a dual lumen configuration proximate the dilatation balloon. Further, these various embodiments depict alternative means for forming the intermediate guide wire port 50 in the two lumen portion of the catheter so that the port extends into the inner or first lumen 20 of the catheter assembly 12. In discussing these similar embodiments, like reference numerals are utilized.

The convertible catheter assembly 12 depicted in FIG. 2 includes a first elongate shaft 14 having a proximal end 17 and a distal end 19 with a lumen 20 extending therethrough. Each of the embodiments of FIGS. 3 and 4 also include these elements.

The proximal-most portion of the first elongate shaft 14 or main tubular member 14 preferably includes a hub assembly 13 (see, FIG. 1) which is depicted schematically in FIGS. 2–4. The hub assembly 13 includes an inflation port 15 which provides fluid communication with the lumen 20. The hub assembly further includes the proximal guide wire port 22 extending therein for slidably receiving a guide wire or stylet 26. As can be seen in FIGS. 2–4, the inflation fluid is injected into a common lumen 20 through the inflation fluid port 15. Therefore, a second seal assembly 60 is included in the guide wire receiving lumen proximal of the inflation fluid port 15. This seal assembly 60 has the guide wire 26 passing therethrough in sealing engagement. The seal assembly 60 prevents leakage of inflation fluid out the proximal end of the main tubular member or first elongate shaft 14. The seal assembly 60 can be an O-ring type seal which frictionally engages the exterior surface of the guide wire 26. Alternative seal designs known in the art may also be utilized. As for example, those disclosed in U.S. Pat. No. 5,490,837 to Blaeser et al., the disclosure of which is incorporated herein by reference. Each of the embodiments of FIGS. 2–4 incorporate this proximal hub design, and are not discussed separately herein.

As depicted in FIG. 2, the first elongate shaft 14 or main tubular member 14 is a single tubular member of generally uniform cross section throughout the length, which extends over the entire length of a catheter. It is, however, recognized that this tubular member may be formed in sections which are joined end-to-end to form a composite tubular member or elongate shaft having a continuous lumen 20 therethrough. Shaft segments may be selected to achieve desired flexibility in their region of choice. The second elongate shaft 30 has a proximal end and a distal end with the shaft disposed coaxially over a distal portion of the first elongate shaft 14, and forming a second lumen 36 therebetween. To form the second lumen 36, the embodiment of FIG. 2 includes a second elongate shaft 30 which is of greater inside diameter than the external diameter of the first elongate shaft 14. Thus, the proximal end 32 of the second elongate shaft 30 is necked down at the point of attachment to the first elongate shaft 14. The proximal end of the second elongate shaft 30 may be adhesively or thermally bonded to the exterior surface of the first elongate shaft. The second elongate shaft 30 extends distally from the proximal point of attachment 32 to the proximal end of the balloon 42. In preferred embodiments, the proximal neck of the balloon is adhesively or thermally secured to the exterior surface of the second elongate shaft 30 so that the interior volume 41 of the balloon is in fluid communication with the second lumen 36.

The embodiments of FIGS. 3 and 4 show an alternative to the design of FIG. 2 for forming the annular lumen 36 in the second elongate shaft 30. The embodiments of FIGS. 3 and 4 incorporate a first elongate shaft 14 which includes a proximal shaft portion of a first diameter and a distal shaft portion of reduced diameter. The reduction in outside diameter of the first elongate shaft 14 occurs distal of the point of attachment 32 of the second elongate shaft 30 so that an annular lumen 36 is formed between the outside surface of the reduced diameter portion of the first elongate shaft 14 and the inside surface of the second elongate shaft 30. As seen in each of FIGS. 2–4, means for fluid communication 70 between the first lumen and second lumen are provided. This can simply include a single or plurality of holes through the wall of the first elongate shaft 20 at the desired location.

Also as shown in each of FIGS. 2–4, a first seal assembly 62 is provided within the first lumen 20 at a location just distal of the means for fluid communication 70 between the first lumen 20 and second lumen 36. As with the second seal assembly 60, the first seal assembly 62 sealingly engages a guide wire 26 extending therethrough to prevent or reduce inflation fluid from passing thereby.

The embodiments of FIGS. 2–4 also depict alternative designs for providing an intermediate guide wire port 50 to be utilized when the catheter assembly 12 is in single operator exchange mode. In the embodiment of FIG. 2, the first elongate shaft 14 proximate the intermediate guide wire port 50 has an outside surface thereof secured to an inside surface of the second elongate shaft 30 over a portion of the length thereof. The intermediate guide wire port 50 is then formed through both the first and second shaft in the secured region. An alternative intermediate guide wire port 50 design is depicted in FIG. 3. In this embodiment, the second elongate shaft 30 has an indentation 51 formed therein over a portion of the sidewall thereof proximate the intermediate guide wire port 50. This allows the outer surface of the first elongate shaft to be affixed to the inner surface of the second elongate shaft at the indentation 51 so that the intermediate guide wire port 50 can be formed through the wall of both elongate tubular members in the affixed region while the first shaft remains coaxial.

A discussion of the operation of the catheter assembly 12 of the present invention in both the single operator exchange mode and the over-the-wire helps provide an understanding of the cooperation of the elements described above in allowing the function of the catheter in the two modes while having only a single proximal lumen 20 over a substantial length of the catheter assembly 12. In the single operator exchange mode, the catheter assembly 12 includes a guide wire or stylet 26 inserted through the first and second seal assemblies so that the distal end of the guide wire 26 terminates distal of the second seal assembly 62, yet proximal of the intermediate guide wire port 50. As assembled, a guide wire (not shown) can be inserted through the intermediate guide wire port 50 and out the distal end of the first lumen 20. When the balloon 40 is placed across a lesion, inflation fluid can be injected through the inflation port 15 and travel distally through the first lumen 20, through the means for fluid communication 70, between the first and second lumen, and into the second lumen 36, which is in fluid communication with the interior volume 41 of the balloon 40 to inflate the balloon. The seal assemblies 60, 62 substantially prevent leakage of inflation fluid out the proximal end of the shaft or distally beyond the second seal assembly 62. Subsequent to placement of the catheter in single operator exchange mode or at any time when operating in this mode, a guide wire can be exchanged by removing the stylet or guide wire 26 and replacing it with the desired guide wire by passing it through the seal assemblies and out the distal end of the catheter.

In over-the-wire mode, operation of the catheter is very similar, however, the guide wire 26 extends over or through the entire length of the catheter and provides additional column support thereto. Again, the seal assemblies 60, 62 allow for inflation of the balloon when desired by preventing leakage of inflation fluid out the proximal end of the catheter or into the guide wire lumen distal of seal 62.

Although the present invention has been described with reference to preferred embodiments, those skilled in the art will recognize that changes may be made in form and detail without departing from the spirit and scope of the invention. As such, it is intended that the foregoing Detailed Description be regarded as illustrative, rather than limiting, and it is the following claims including all equivalents thereof, which are intended to define the scope of the invention.

What is claimed is:

1. A convertible catheter assembly having a single proximal lumen comprising:

(a) a first elongate shaft having a proximal end and a distal end with a first lumen extending therethrough, said proximal end having a proximal guide wire port for slidably receiving a guide wire or stylet into said first lumen;

(b) a second elongate shaft, having a proximal end and a distal end, disposed over a distal portion of said first elongate shaft and forming a second lumen therebetween, said second elongate shaft sealingly engaging said first elongate shaft proximate the proximal end of said second elongate shaft;

(c) an inflatable balloon having a proximal end sealingly connected proximate the distal end of said second elongate shaft and a distal end sealingly connected proximate the distal end of said first elongate shaft;

(d) means for fluid communication between said first lumen and said second lumen;

(e) a seal assembly disposed within said first lumen distal of said means for fluid communication between said first and said second lumen; said seal assembly sized to slidably receive said guide wire or stylet therethrough; and, (f) an intermediate guide wire port distal of said seal assembly providing an access point for a guide wire into said first lumen.

2. The catheter assembly of claim 1, wherein said first elongate shaft proximate said intermediate guide wire port has an outside surface thereof secured to an inside surface of said second elongate shaft over a portion of the length thereof and said intermediate guide wire port is formed through both said first and said second shaft in said secured region.

3. The catheter assembly of claim 1, wherein said second elongate shaft has an indentation formed therein over a portion of the side wall thereof proximate said intermediate guide wire port so that an outer surface of said first elongate shaft is affixed to an inner surface of said second elongate shaft at said indentation and said intermediate guide wire port is formed through the wall of both elongate shafts in said affixed region.

4. The catheter assembly of claim 1, wherein said means for fluid communication between said first lumen and said second lumen include at least one hole through the side wall of said first elongate shaft distal of said proximal end of said second elongate tubular shaft and proximal of said seal assembly.

5. The catheter assembly of claim 4, wherein said first elongate shaft has a proximal region of a first outside diameter and a distal region of reduced outside diameter, said distal region of reduced diameter being distal of the proximal end of said second elongate shaft so that an annular lumen is formed between said second elongate shaft and said reduced diameter portion of said first elongate shaft while maintaining the overall profile of said catheter assembly relatively constant over its entire length.

6. The catheter assembly of claim 1, wherein said seal assembly comprises an o-ring type seal fixed within said first lumen which forms a friction seal with a guide wire or stylet placed therethrough.

7. The catheter assembly of claim 6, wherein said first seal assembly comprises an o-ring type seal fixed within said lumen which forms a friction seal with a guide wire or stylet placed therethrough.

8. The catheter assembly of claim 1, further comprising a stylet extending into the proximal end thereof through said seal assembly and forming a seal therewith.

9. A convertible catheter assembly having a single proximal lumen comprising:

(a) a first elongate shaft having a proximal end and a distal end with a first lumen extending therethrough, said proximal end having a proximal guide wire port for slidably receiving a guide wire or stylet into said first lumen and an inflation fluid receiving port in fluid communication with said first lumen;

(b) a first seal assembly proximal of said inflation fluid receiving port, said first seal assembly slidably receiving said guide wire or stylet therethrough when extended through said proximal guide wire port;

(c) a second elongate shaft, having a proximal end and a distal end, coaxially disposed over a distal portion of said first elongate shaft and forming a second lumen therebetween, said second elongate shaft sealingly engaging said first elongate shaft proximate the proximal end of said second elongate shaft;

(d) an inflatable balloon having a proximal end sealingly connected proximate the distal end of said second elongate shaft and a distal end sealingly connected proximate the distal end of said first elongate shaft;

(e) means for fluid communication between said first lumen and said second lumen;

(f) a second seal assembly disposed within said first lumen distal of said means for fluid communication between said first and said second lumen; said second seal assembly sized to slidably receive said guide wire or stylet therethrough; and, (g) an intermediate guide wire port distal of said second seal assembly providing an access point for a second guide wire into said first lumen.

10. The catheter assembly of claim 9, wherein said first elongate shaft proximate said intermediate guide wire port has an outside surface thereof secured to an inside surface of said second elongate shaft over a portion of the length thereof and said intermediate guide wire port is formed through both said first and said second shaft in said secured region.

11. The catheter assembly of claim 9, wherein said second elongate shaft has an indentation formed therein over a portion of the side wall thereof proximate said intermediate guide wire port so that an outer surface of said first elongate shaft is affixed to an inner surface of said second elongate shaft at said indentation and said intermediate guide wire port is formed through the wall of both elongate tubular members in said affixed region.

12. The catheter assembly of claim 9, wherein said means for fluid communication between said first lumen and said second lumen include at least one hole through the side wall of said first elongate shaft distal of said proximal end of said second elongate shaft and proximal of said second seal assembly.

13. The catheter assembly of claim 12, wherein said first elongate shaft has a proximal region of a first outside diameter and a distal region of reduced outside diameter, said change in diameter distal of the proximal end of said second elongate shaft so that an annular lumen is formed between said second elongate shaft and said reduced diameter portion of said first elongate shaft while maintaining the overall profile of said catheter assembly relatively constant over its entire length.

14. The catheter assembly of claim 9, wherein said second seal assembly comprises an o-ring type seal fixed within said first lumen which forms a friction seal with a guide wire or stylet placed therethrough.

15. The catheter assembly of claim 14, wherein said first seal assembly comprises an o-ring type seal fixed within said first lumen which forms a friction seal with a guide wire or stylet placed therethrough.

16. The catheter assembly of claim 9, further comprising a stylet extending into the proximal end thereof through said first and said second seal assemblies and forming a seal therewith.

17. An intravascular catheter assembly comprising:

(a) a main tubular member having a proximal end and a distal end with a lumen extending therethrough;

(b) a first seal assembly proximate the proximal end of said main tubular member, said first seal assembly slidably receiving a guide wire or stylet therethrough into said lumen of said main tubular member forming a proximal guide wire port;

(c) an inflation fluid port proximate the proximal end of said main tubular member in fluid communication with said lumen of said main tubular member, said inflation fluid port distal of said first seal assembly;

(d) a distal outer tubular member having a proximal end and a distal end with a lumen extending therethrough, said distal outer tubular member coaxially disposed over said main tubular member with the proximal end of said distal outer tubular member secured to the outer surface of said main tubular member with said distal outer tubular member extending distally therefrom;

(e) an inflatable balloon having a proximal end secured to said distal outer tubular member proximate the distal end thereof and a distal end secured to said main tubular member proximate the distal end thereof, said balloon defining an internal volume in fluid communication with said distal outer tubular member lumen;

(f) means for fluid communication between said lumen of said main tubular member and said lumen of said distal outer tubular member;

(g) a second seal assembly disposed within said lumen of said main tubular member distal of said means for fluid communication between said lumen of said main tubular member and said lumen of said outer tubular member, said second seal assembly slidably receiving said guide wire or stylet therethrough; and, (h) an intermediate guide wire port distal of said second seal, said intermediate guide wire port in fluid communication with the lumen of said main tubular member providing an access for a second guide wire through the wall of both said main tubular member and said distal outer tubular member at said access.

18. The catheter assembly of claim 17, wherein said main tubular member proximate said intermediate guide wire port has an outside surface thereof secured to an inside surface of said distal outer tubular member over a portion of the length thereof and said intermediate guide wire port is formed through both said main tubular member and said distal outer tubular member in said secured region.

19. The catheter assembly of claim 17, wherein said distal outer tubular member has an indentation formed therein over a portion of the side wall thereof proximate said intermediate guide wire port so that an outer surface of said main tubular member is affixed to an inner surface of said distal outer tubular member at said indentation and said intermediate guide wire port is formed through the wall of both tubular members in said affixed region.

20. The catheter assembly of claim 17, wherein said means for fluid communication between said main tubular member lumen and said distal outer tubular member lumen include at least one hole through the side wall of said main tubular member distal of said proximal end of said distal outer tubular member and proximal of said second seal assembly.

21. The catheter assembly of claim 20, wherein said main tubular member has a proximal region of a first outside diameter and a distal region of reduced outside diameter, said distal region of reduced outside diameter being distal of the proximal end of said distal outer tubular member so that an annular lumen is formed between said distal outer tubular member and said reduced diameter region of said main tubular member while maintaining the overall profile of said catheter assembly relatively constant over its entire length.

22. The catheter assembly of claim 17, wherein said second seal assembly comprises an o-ring type seal fixed within said main tubular member lumen which forms a friction seal with a guide wire or stylet placed therethrough.

23. The catheter assembly of claim 22, wherein said first seal assembly comprises an o-ring type seal fixed within said main tubular member lumen which forms a friction seal with a guide wire or stylet placed therethrough.

24. The catheter assembly of claim 23, further comprising a stylet extending into the proximal end thereof through said first and said second seal assemblies and forming a seal therewith.

\* \* \* \* \*